US009649201B2

(12) United States Patent
Stuchin

(10) Patent No.: US 9,649,201 B2
(45) Date of Patent: May 16, 2017

(54) ANATOMIC SOCKET ALIGNMENT GUIDE AND METHODS OF MAKING AND USING SAME

(71) Applicant: NEW YORK UNIVERSITY, New York, NY (US)

(72) Inventor: Steven A. Stuchin, New York, NY (US)

(73) Assignee: NEW YORK UNIVERSITY, New York, NY (US)

(*) Notice: Subject to any disclaimer, the term of this patent is extended or adjusted under 35 U.S.C. 154(b) by 490 days.

(21) Appl. No.: 14/363,846

(22) PCT Filed: Dec. 7, 2012

(86) PCT No.: PCT/US2012/068416
§ 371 (c)(1),
(2) Date: Jun. 9, 2014

(87) PCT Pub. No.: WO2013/086300
PCT Pub. Date: Jun. 13, 2013

(65) Prior Publication Data
US 2014/0336661 A1 Nov. 13, 2014

Related U.S. Application Data

(60) Provisional application No. 61/568,345, filed on Dec. 8, 2011.

(51) Int. Cl.
*A61F 2/46* (2006.01)
*A61F 2/30* (2006.01)
*G06F 17/50* (2006.01)

(52) U.S. Cl.
CPC ........ *A61F 2/4609* (2013.01); *A61F 2/30942* (2013.01); *G06F 17/50* (2013.01); *A61F 2002/30948* (2013.01); *A61F 2002/30952* (2013.01); *A61F 2002/4632* (2013.01); *A61F 2002/4687* (2013.01)

(58) Field of Classification Search
CPC ........... A61B 17/1742; A61B 2017/568; A61F 2/4609; A61F 2/30942
See application file for complete search history.

(56) References Cited

U.S. PATENT DOCUMENTS

| 4,792,337 A | 12/1988 | Muller |
| 5,376,125 A | 12/1994 | Winkler |
| 7,076,980 B2 | 7/2006 | Butscher et al. |
| 7,245,977 B1 | 7/2007 | Simkins |

(Continued)

OTHER PUBLICATIONS

Ono et al., "Method for Preparing an Exact-Size Model Using Helical Volume Scan Computed Tomography," Plast. Reconstr. Surg. (1994) 93(7):1363-1371.
Robiony et al., "Viirtual Reality Surgical Planning for Maxillofacial Distraction Osteogenesis: The Role of Reverse Engineering Rapid Prototyping and Cooperative Work," J. Oral Maxillofac. Surg. (2007) 65:1198-1208.

(Continued)

*Primary Examiner* — Andrew Yang
(74) *Attorney, Agent, or Firm* — John M. Garvey; DLA Piper LLP (US)

(57) ABSTRACT

This disclosure provides an anatomic socket alignment guide set, for total hip replacement arthroplasty. The guide set is created from patient-specific medical images, allowing the guide set components to recreate the native center of rotation of a patient's hip joint, thereby permitting accurate placement of the hip replacement prosthesis.

15 Claims, 6 Drawing Sheets

(56) References Cited

U.S. PATENT DOCUMENTS

| | | | |
|---|---|---|---|
| 7,967,868 B2 | 6/2011 | White et al. | |
| 8,070,752 B2 | 12/2011 | Metzger et al. | |
| 8,608,749 B2 * | 12/2013 | Meridew | A61B 17/151 |
| | | | 606/91 |
| 8,998,909 B2 * | 4/2015 | Gillman | A61F 2/30942 |
| | | | 606/87 |
| 9,526,514 B2 * | 12/2016 | Kelley | A61F 2/4609 |
| 2005/0148843 A1 * | 7/2005 | Roose | A61B 17/17 |
| | | | 600/407 |
| 2009/0149977 A1 | 6/2009 | Schendel | |
| 2009/0163922 A1 | 6/2009 | Meridew et al. | |
| 2011/0190775 A1 * | 8/2011 | Ure | A61F 2/4609 |
| | | | 606/91 |
| 2012/0289965 A1 * | 11/2012 | Gelaude | A61B 17/15 |
| | | | 606/87 |
| 2013/0245631 A1 * | 9/2013 | Bettenga | A61B 17/1666 |
| | | | 606/91 |
| 2013/0338673 A1 * | 12/2013 | Keppler | A61B 17/1778 |
| | | | 606/96 |
| 2014/0142578 A1 * | 5/2014 | Hananouchi | A61B 17/1746 |
| | | | 606/87 |

OTHER PUBLICATIONS

Swann, "Integration of MRI and Stereolithography to Build Medical Models. A Case Study," Rapid Prototyping J. 1996; 2:41-46.
International Search Report and Written Opinion, PCT/US2012/068416, dated Mar. 29, 2013 (14 pages).

* cited by examiner

ANATOMIC SOCKET ALIGNMENT GUIDE AND METHODS OF MAKING AND USING SAME

CROSS REFERENCE TO RELATED APPLICATIONS

This application is the U.S. national phase application of International Patent Application No. PCT/US12/68416, entitled "Anatomic Socket Alignment Guide and Methods of Making and Using Same," filed on Dec. 7, 2012, which claims priority to and the benefit of U.S. Provisional Patent Application Ser. No. 61/568,345 entitled "Anatomic Socket Alignment Guide and Methods of Making and Using Same," which was filed on Dec. 8, 2011. The entirety of the aforementioned applications is herein incorporated by reference.

FIELD OF THE INVENTION

This disclosure is in the field of orthopedic medicine. More specifically, this disclosure is related to an anatomic socket alignment guide set, for total hip replacement arthroplasty.

BACKGROUND

Correct positioning of the socket in total hip replacement arthroplasty is difficult to achieve, using currently available jigs and alignment guides. Such variables as, for example patient positioning on the operating table, anatomic issues including patient-to-patient variability, and questions of parallax, all must be considered in the surgeon's judgment at the time of the arthroplasty procedure. Any resultant inaccuracies can threaten hip stability and durability. While surgical navigation may address some of these problems, this approach is not universally available, and adds both expense and time to the procedure, which also lengthens the concomitant time a patient is subject to the risks of anesthesia. Accordingly, there remains a need in the surgical arts, for improved alignment guides that can aid a surgeon in a total hip replacement arthroplasty procedure, improving the precision of the procedure and enhancing surgical outcome.

DETAILED DESCRIPTION

Figure 1:
FIG. 1 illustrates the positioning guide of the guide set.

Current patient imaging techniques such as MRI and CT scans, provide high-definition three-dimensional maps of patient joints and tissues. Anatomical structures can be resolved to sub-millimeter levels based on MRI imaging technologies in widespread availability, and high spectral and spatial resolution (HiSS) systems promise even greater resolution. While current imaging technologies deliver better information to the surgeon, allowing informed decisions prior to the surgery, these technologies still do not substitute for the surgeon's skill when performing the total hip replacement arthroplasty. However, high resolution mapping technologies provide the basis for creating anatomically matched guides.

Current commercial efforts have resulted in patient-specific cutting blocks for knee replacements (see, for example Signature (Biomet); Visionaire (Smith & Nephew); and Patient Specific Instrument (Zimmer) systems). In knee replacement procedures, anatomically configured preformed cutting jigs allow for a planar cut with the possibility of indicating rotation in the same plane. However, for hip replacement procedures, the efforts are complicated in that the acetabulum requires the two rotational axes of abduction and anteversion.

The present disclosure provides patient-specific guides, derived from high-resolution anatomical images of the patient obtained through common imaging techniques known in the medical arts. Imaging devices appropriate for the present invention include x-ray devices, MRI or ultrasound equipment, or similar means of generating patient-specific imaging data. Patient-specific data used to generate such a virtual model can be obtained from one or more patient data sources. The data is rendered e.g., by computer using standard computer aided design (CAD) or animation modeling software, to produce detailed three-dimensional anatomical models of the patient, for specific surgical sites (e.g., the hip joint), which are further processed e.g., by computer aided manufacturing (CAM) systems. The CAM system accesses the data specifying the virtual model, as configured and finalized by the operator, then transforms the model into thin, virtual, horizontal cross-sections, which it uses to create successive layers to fabricate a physical model, for example using additive manufacturing techniques, such as rapid prototyping, stereolithography, or other similar technologies. Such techniques are described in greater detail by M. Robiony el al., "Cranio-Maxillofacial Bone Surgery," *J. Oral Maxfac. Surg.* (2007) 1198-1208; Ono I et al., "Method for Preparing an Exact-Size Model Using Helical Volume Scan Computed" *Plast. Reconstr. Surg.* (1994) 93: 1363; S. Swan, "Integration of MRI and Stereolithography to Build Medical Models. A Case Study," *Rapid Prototyping Journal*, (1996) 2:41; H. P. Wolf et al., "High Precision 3-D Model Design Using CT and Stereolithography," CAS (1994) 1:46. See also, Schendel, S., Methods, Systems, And Computer Program Products for Shaping Medical Implants Directly from Virtual Reality Models, U.S. Ser. No. 12/263,309; as well as U.S. Pat. No. 7,245,977 to Simkins, and U.S. Pat. No. 7,076,980 to Butscher et al.

An exemplary system according to some embodiments, includes at least one modeling server that is communicatively coupled to one or more clients by a communications infrastructure. Clients can be represented by a variety of devices, such as but not limited to, personal computers, personal digital assistants, or smart phones. Clients can include one or more output mechanisms that output information to the user (e.g., physician, surgeon, clinician, technician, and other medical professionals). Such output mechanisms include but are not limited to a monitor, an LCD screen, or a printer. One or more input mechanisms can be included to permit a user to input information to the clients. Such input mechanisms include a keyboard, a mouse, a stylus, etc. Clients can include client software such as web browser software. The web browser software can include a browser program, such as the MICROSOFT®

INTERNET EXPLORER® browser application. For example, clients can access the software tools, patient data, or other information residing on the modeling server or other system components via the web browser software when the communications infrastructure includes the global-based Internet. The web browser software can include a plug-in, applet or similar executable process. A plug-in can be obtained from the modeling server or from a third party. Alternatively, plug-ins can be pre-installed on clients. Clients include network interface hardware and software that allows the client to transmit and receive data over communications infrastructure. Communications infrastructure can be a wired and/or wireless local area network (LAN), virtual LAN (VLAN), wide area network (WAN), and/or metropolitan area network (MAN), such as an organization's intranet, a local internet, the global-based Internet (including the World Wide Web (WWW)), an extranet, a virtual private network (VPN), licensed wireless telecommunications spectrum for digital cell (including CDMA, TDMA, GSM, EDGE, GPRS, CDMA2000, WCDMA FDD and/or TDD or TD-SCDMA technologies). Communications infrastructure can support wired, wireless, or combinations of both transmission media, including satellite, terrestrial (e.g., fiber optic, copper, UTP, STP, coaxial, hybrid fiber-coaxial (HFC), or the like), radio, free-space optics, and microwave transmission.

The modeling server includes a set of computer-executable instructions that cause a computer to visualize and manipulate a virtual reality model. The instructions may be executed at the modeling server and interactive images of the virtual model can be transmitted to the clients, or alternatively, an application program can be distributed to a client, so that the interactive visualization operations can be executed on the local client. The software instructions include a set of functions or routines that cause the user interface for a client to display a high-resolution, three-dimensional representation of a patient's anatomical structures, and provide the medical professional with tools for visualizing and analyzing the virtual model. Virtual cutting and shaping tools allow the medical professional to segment the model by showing slices or sections through the model at arbitrary, user-defined planes. For example, the visualization tools include routines and functions for simulating changes in the anatomical position or shape of an anatomical structure. The elements of the anatomical structure can be analyzed quickly in either static format (e.g., no movement of the anatomical structures relative to each other) or in a dynamic format (e.g., during movement of anatomical structures relative to each other, such as during abduction and anteversion of the leg, etc.).

The medical professional logs in to a defined web site, accesses a file containing the patient's imaging data, and then he or she uses the interactive visualization tools of the modeling server to plan the procedure and simulate the results. In one embodiment, a web-based system is provided to import the patient-specific data in the standard Digital Imaging and Communications in Medicine (DICOM) format. In another embodiment, an Active X control program is used to support data acquisition from medical images, and permit segmentation, visualization, integrated surface and volume rendering and simulation. Upon configuring and finalizing the virtual model, a fabrication system accesses the specification data for the virtual model from client or modeling server depending on which component contains the application for visualizing and finalizing the design of the guides.

It will be appreciated that the guides according to the present invention, will conform only in part to various features of the patient's anatomy. Other surfaces on the guide provide for features that imbue functionality to the guide but are not in contact with the patient and do not need to conform to the patient's anatomy. Accordingly, the guides of the present disclosure contain both patient-conforming and non-conforming regions. Patient conforming regions are specific to the anatomy of the patient. Non-conforming regions may take any suitable morphology that does not interfere with their functionality, i.e., positioning, aligning and inserting of a prosthetic hip socket device.

Figure 2:
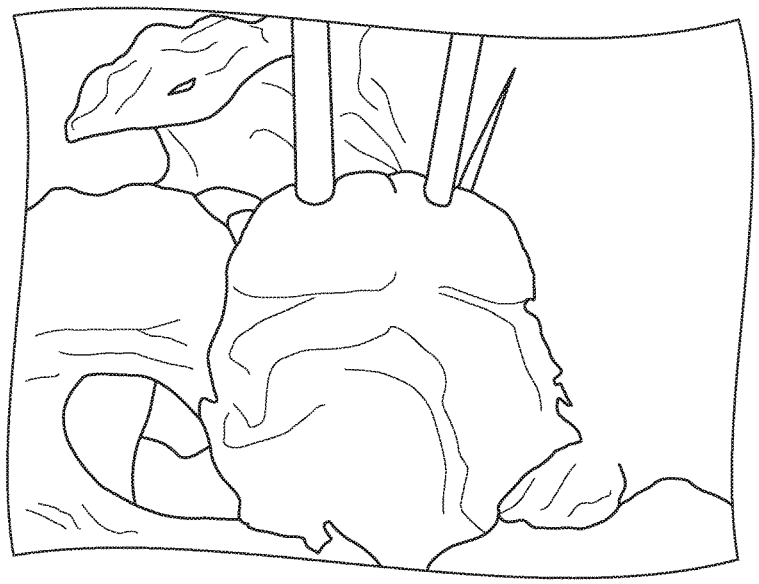
FIG. 2 shows the positioning guide aligned within the acetabulum of a human patient. Guide pins extend through the positioning guide at reference locations on the pelvis.
Figure 6:
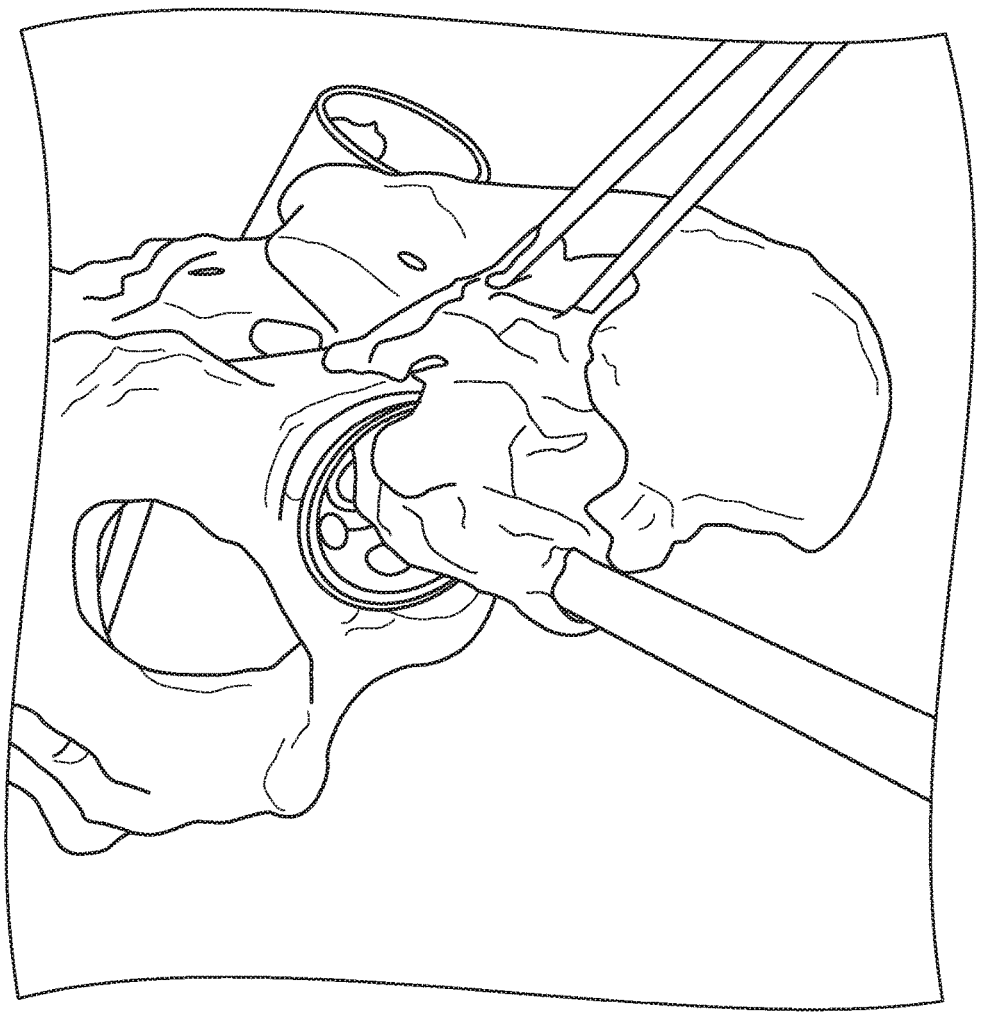
FIG. 6 shows the insertion guide having an acetabular socket prosthesis, aligned centrally to the acetabulum.

In a representative embodiment, the invention provides an orthopedic device set for total hip replacement arthroplasty procedures. The device set includes both a positioning guide and an insertion guide. The positioning guide, shown in FIG. 1, has a first surface substantially conforming to a patient's native acetabulum. In practice, the femur head is dislocated from the acetabulum during a total hip replacement procedure. The positioning guide is then placed within the acetabulum such that the first (conforming) surface engages the acetabular surface, and the unique morphology and features of the patient's anatomy secure the guide. Distal to the first surface is a second surface, which is external to the acetabulum. The second surface substantially conforms to a region on the patient's native pelvis, and it engages the pelvic bone. The positioning guide "fits" and is therefore removably secured within the patient's acetabulum and at a region external to the acetabular notch. The positioning guide has at least one aperture through the second surface, defining positioning guide reference locations. There are two through-holes defining reference locations, shown in FIG. 1. These reference locations provide orientation positions on the patient's pelvis, which in conjunction with the insertion guide, shown in FIG. 4, facilitate subsequent socket alignment and insertion, as shown in FIG. 6. For example, the reference locations define the site of placement for surgical guide pins, which are inserted into the pelvis prior to removal of the positioning guide as shown in FIG. 2. One will appreciate that the "apertures" on the second surface of the positioning guide need not be limited to through-holes in this surface. It is sufficient that the second surface present enough material to permit secure placement of the guide pins or other reference markers. For example, a "U" shaped notch-contained on three sides but open on a fourth side, would permit surgical guide pin placement while facilitating positioning guide removal in a manner that does not disturb the guide pins. The guide pins can also serve as a reference for other types of guides, e.g., a leg length caliper may be affixed to one of the pins for intraoperative leg length determination. One of skill in the art will also appreciate, that the term "guide pins" exemplifies one potential means of identifying and securing surgical tools at a site; other means are deemed within the scope of this invention and will be apparent in view of the teachings provided.

Figure 3:
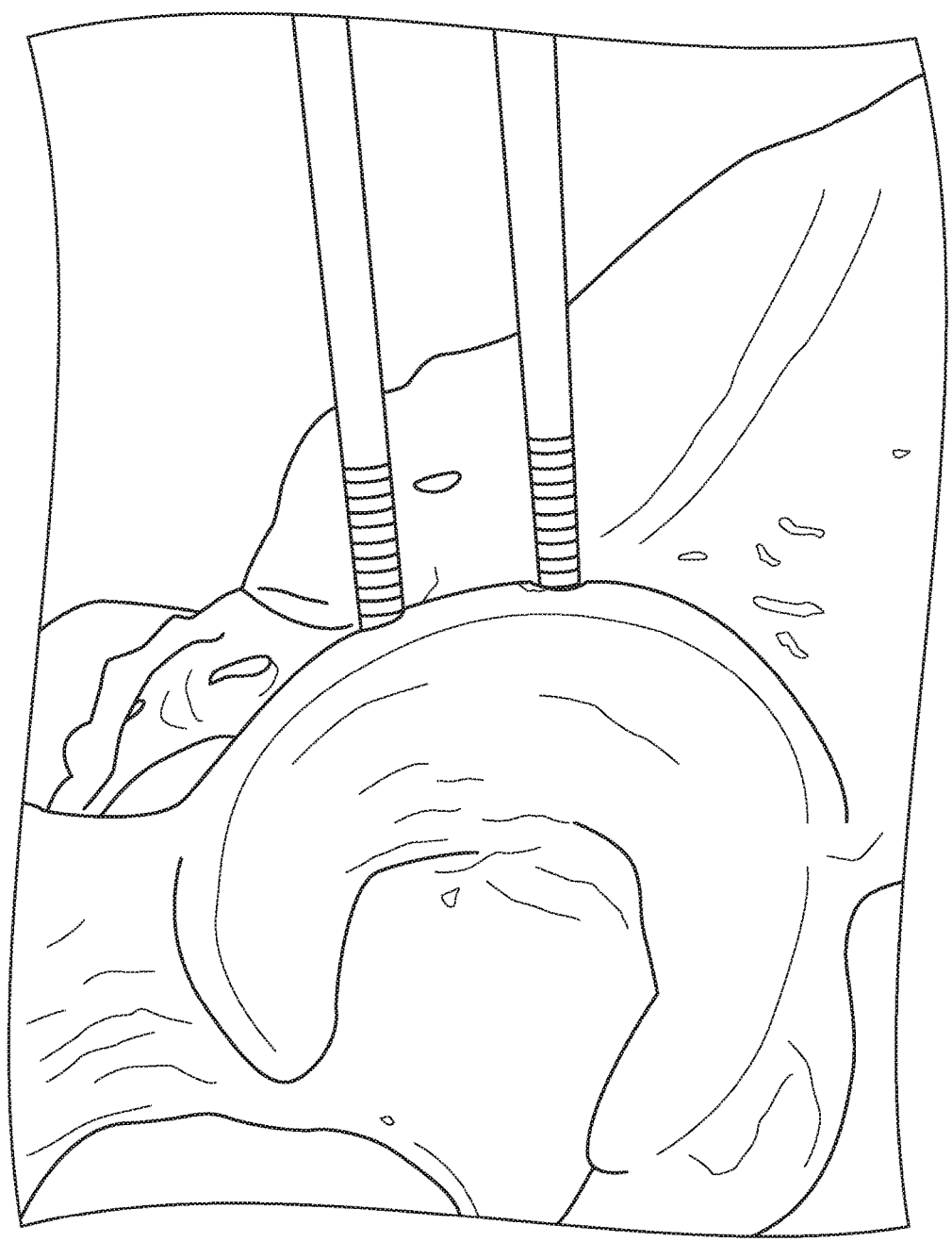
FIG. 3 shows the pelvis with the positioning guide removed and the guide pins in place.
Figure 4:
FIG. 4 illustrates the insertion guide of the guide set.

Following placement of guide pins, the positioning guide is removed resulting in a secure reference point from which the surgeon may base further decisions, such as leg length and axis of rotation for the hip joint as described herein. This is shown in FIG. 3. The insertion guide is applied next. This first surface of the insertion guide overlaps in-part with the same region on the patient's pelvis as the positioning guide, though it does not need to conform to the patient's pelvis. Specifically, the overlap is defined by the area including the positioning guide reference locations. The positioning guide serves to place guide pins, and the guide pins are further used to position the insertion guide. Accordingly, the first surface of the positioning guide includes one or more securing features positioned such that the securing features are equidistant relative to the positioning guide second surface reference locations. As shown in FIG. 4, the insertion guide first surface has securing features as exemplified by two through-holes positioned in the same relative locations as the positioning guide shown in FIG. 1. The through-holes permit secure but removable affixation of the insertion guide to the pins. Other types of structures such as a "U" shaped notch structure, which may further include features at the distal/open portions of the notch that can engage the guide pins, will be evident to those of skill in the art. However, it is useful if such securing features permit tight adherence between the insertion guide and pins, and the securing features "lock" the insertion guide into position. In one embodiment, the insertion guide has a first surface which does not conform to the patient's pelvis; the positioning guide positions the pins; and then the pins position the insertion guide, which therefore does not need to conform to any pelvic anatomy. In other embodiments, the insertion guide includes a first surface that conforms to the patient's pelvic anatomy. In such embodiments, since one side of the first surface of the insertional device conforms to the patient's pelvis, the patient's own anatomical features assist in aligning and securing the insertion guide.

Figure 5:
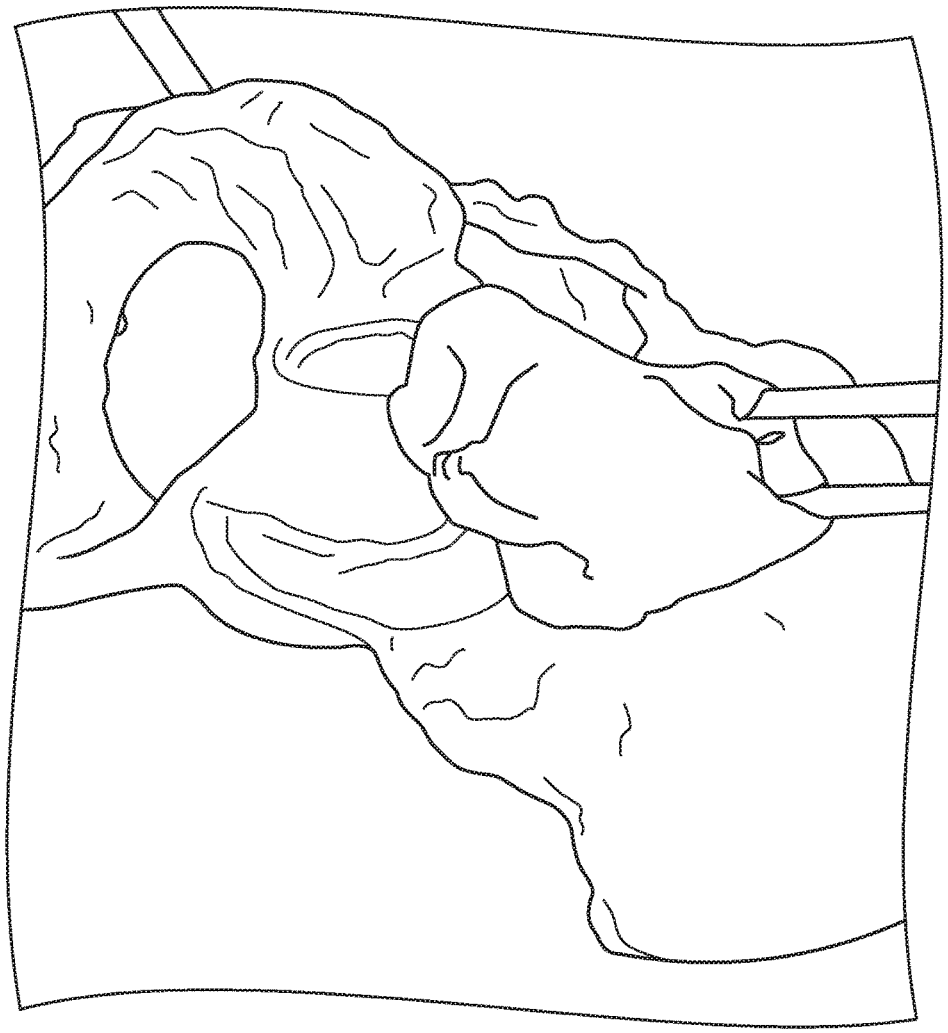
FIG. 5 shows the insertion guide affixed to the guide pins in a cut-away view, illustrating the acetabulum of the patient.

The insertion guide has a second surface distal to the first surface, the second surface having an aperture therethrough, the aperture being offset from the securing features by a patient-specific distance such that the midpoint of the aperture aligns centrally with the acetabulum of the patient. This is shown in FIG. 5 where the insertion device is affixed to the patient's pelvis. The second surface is not shown in order to permit visualization of the device relative to the acetabulum. This distance from the pins at the reference locations to the center of the patient's acetabulum varies from individual-to-individual, and is calculated with precision based on the patient's hip joint images; and based on such distance, the three-dimensional model and patient-specific surgical guide set is obtained as described above. The insertional guide aligns the socket insertional prosthetic device. If the logic determining creation of the guide set is based on the center of rotation, and the line that is its three-dimensional axis determines e.g., abduction, anteversion and medialization, then small differences in socket dimension or depth of reaming (of the acetabulum) will not cause significant problems, allowing for the surgeon to take into account bone density and reaming choices. The positioning guide determines cup abduction and anteversion. As the center of the cup remains the same no matter the outer diameter, the guide set needn't be determinative of cup size.

The insertion guide may optionally include a third surface located distal to the aperture of the second surface at a distance defined by the radius of an acetabular socket prosthesis, the third surface further having an annular depression of sufficient size and depth to engage removably a portion of the acetabular socket prosthesis. Since the guide set is custom-created for each patient, it is a simple matter to determine the appropriate socket for use in that patient, and design the insertion guide to accommodate the exact size of the socket desired.

Continuing with the above example, where the positioning guide has been used to set reference guide pins, and the insertion guide has been placed into position based on these reference guide pins, the socket prosthesis is then introduced into the reamed acetabulum as shown in FIG. 6. The socket prosthesis is loaded into the insertional guide, with the outer circumference of the socket removably engaging the third surface of the insertional device. The configuration of the guide around the socket determines the limits of abduction and anteversion in the repaired joint. A push rod is inserted through the aperture of the second surface. This push rod aligns centrally in the socket, and when articulated, permits precise deposition of the socket into the reamed acetabulum. In certain embodiments, the push rod has a depth-stop feature, for example a geometric feature that engages or is otherwise stopped by the second surface of the insertion guide.

While the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims. All references and patent documents cited herein are hereby incorporated by reference in their entirety.

The invention claimed is:

1. An orthopedic device set comprising:
 a positioning guide having:
  a first surface substantially conforming to a patient's native acetabulum; and
  a second surface distal to the first surface, the second surface substantially conforming to a region of the patient's native pelvis and comprising one or more apertures therethrough defining positioning guide reference locations; and
 an insertion guide having:
  a first surface comprising one or more securing features positioned such that the securing features are equidistant relative to the positioning guide second surface reference locations;
  a second surface distal to the first surface, the second surface having an aperture therethrough, the aperture being offset from the securing features by a patient-specific distance such that the aperture aligns centrally with the acetabulum of the patient; and
  a third surface located distal to the aperture of the second surface at a distance defined by the radius of an acetabular socket prosthesis, the third surface further comprising an annular depression of sufficient size and depth to engage removably a portion of the acetabular socket prosthesis.

2. The orthopedic device set of claim 1, wherein the insertion guide aperture is offset at a distance that is the center of rotation of the patient's native hip joint.

3. The orthopedic device set of claim 1, further comprising one or more guide pins having a thickness no greater than the positioning guide aperture(s).

4. The orthopedic device set of claim 3, further comprising a leg length caliper having a proximal end with a guide pin attachment means.

5. The orthopedic device set of claim 1, further comprising an acetabular socket prosthesis insertional device.

6. The orthopedic device set of claim 5, wherein the insertional device further comprises a feature larger than the diameter of the insertion guide aperture, the feature positioned distal to the acetabular socket prosthesis insertional device at a point defining the limit of insertion for the acetabular socket prosthesis.

7. A surgical kit comprising: the device set of claim 1, which is sterile, and further comprising appropriate packaging and instructions for use of the device set.

8. A method of manufacturing an orthopedic device set comprising:
   obtaining a three-dimensional image of a hip joint of a patient, and rendering from the three-dimensional image a device set further comprising:
   a positioning guide having:
      a first surface substantially conforming to a patient's native acetabulum, and
      a second surface distal to the first surface, the second surface substantially conforming to a region of the patient's native pelvis and comprising one or more apertures therethrough defining positioning guide reference locations; and
   an insertion guide having:
      a first surface comprising one or more securing features positioned such that the securing features are equidistant relative to the positioning guide second surface reference locations;
      a second surface distal to the first surface, the second surface having an aperture therethrough, the aperture being offset from the securing features by a suitable distance such that the aperture aligns centrally to the acetabulum of a patient as determined from the three-dimensional image of the patient with reference to the positioning guide reference locations; and
      a third surface located distal to the aperture of the second surface at a distance defined by the radius of an acetabular socket prosthesis, the third surface further comprising an annular depression of sufficient size and depth to engage removably a portion of the acetabular socket prosthesis selected for the patient.

9. The method of claim 8, comprising obtaining the image through CT or MRI imaging techniques.

10. The method of claim 8, comprising rendering the positioning and insertion guides by a computer using image-based modeling and sculpting software with an automated sculpting device controlled by the computer.

11. A surgical method, comprising:
   identifying a patient in need of hip surgery requiring a hip prosthesis;
   imaging the hip joint of the patient;
   obtaining the patient-specific device set of claim 1; and
   performing hip replacement surgery on the patient, the surgery comprising:
      orienting and placing the positioning guide within the patient's native acetabulum;
      securing one or more guide pins to the pelvic bone of the patient at locations defined by the one or more positioning guide reference points;
      withdrawing the first guide device from the acetabulum while leaving the guide pins in position, then reaming the acetabulum of the patient;
      securing the insertion guide to the one or more guide pins;
      removably securing to the insertion guide, an acetabular socket prosthesis, such that the prosthesis, when secured by the insertion guide, is aligned centrally to the reamed acetabulum of the patient as determined from the three-dimensional image of the native acetabulum of the patient with reference to the positioning guide reference locations; and
      inserting the socket prosthesis into the reamed acetabulum at a depth and orientation such that native abduction and anteversion of the hip joint is substantially preserved.

12. The method of claim 11, comprising affixing a leg length caliper to the guide pins following removal of the positioning guide.

13. The method of claim 11, comprising obtaining the image through CT or MRI imaging techniques.

14. The method of claim 11, comprising obtaining the patient-specific device set by rendering the positioning and insertion guides by a computer using image-based modeling and sculpting software with an automated sculpting device controlled by the computer.

15. A surgical kit comprising: the device set of claim 6, which is sterile, and further comprising appropriate packaging and instructions for use of the device set.

* * * * *